(12) United States Patent
Allum

(10) Patent No.: US 10,859,456 B2
(45) Date of Patent: *Dec. 8, 2020

(54) TECHNIQUES FOR DETERMINING PATIENT AIRWAY PRESSURE

(71) Applicant: SILVERBOW DEVELOPMENT, LLC, San Ramon, CA (US)

(72) Inventor: Todd Allum, Livermore, CA (US)

(73) Assignee: INOGEN, INC., Goleta, CA (US)

( * ) Notice: Subject to any disclaimer, the term of this patent is extended or adjusted under 35 U.S.C. 154(b) by 239 days.

This patent is subject to a terminal disclaimer.

(21) Appl. No.: 16/006,699

(22) Filed: Jun. 12, 2018

(65) Prior Publication Data

US 2018/0364119 A1 Dec. 20, 2018

Related U.S. Application Data

(63) Continuation of application No. 14/517,186, filed on Oct. 17, 2014, now Pat. No. 9,995,645.

(Continued)

(51) Int. Cl.
*G01L 7/00* (2006.01)
*A61M 16/06* (2006.01)
(Continued)

(52) U.S. Cl.
CPC ........... *G01L 7/00* (2013.01); *A61M 16/0051* (2013.01); *A61M 16/024* (2017.08);
(Continued)

(58) Field of Classification Search
CPC ............. A61M 16/00; A61M 16/0051; A61M 16/0063; A61M 16/0096; A61M 16/024; A61M 16/026; A61M 16/0666; A61M 16/0672; A61M 16/0677; A61M 16/085; A61M 16/0858; A61M 16/0875;
(Continued)

(56) References Cited

U.S. PATENT DOCUMENTS 5,551,419 A  9/1996 Froehlich et al.
6,478,026 B1  11/2002 Wood
(Continued)

FOREIGN PATENT DOCUMENTS

FR  2 250 541 A1  6/1975
WO  2011/029074 A1  3/2011

*Primary Examiner* — Joseph D. Boecker
(74) *Attorney, Agent, or Firm* — Artegis Law Group, LLP

(57) ABSTRACT

A ventilator is configured to assist a user with breathing, while eliminating the need for extraneous sensors and tubing normally found in prior art ventilators. The ventilator relies on a predetermined relationship between a measurable quantity associated with a compressed gas and the maximum pressure of that compressed gas upon delivery to the user. The measurable quantity may be mass flow rate of the compressed gas or pressure within a delivery lumen used to transport the compressed gas, among others. Based on the predetermined relationship, the control logic within the ventilator determines whether the pressure of compressed gas delivered to the user exceeds a maximum allowable pressure. When the maximum pressure is exceeded, the control logic initiates corrective action to reduce the pressure of the compressed gas.

20 Claims, 5 Drawing Sheets

Related U.S. Application Data

(60) Provisional application No. 61/893,000, filed on Oct. 18, 2013.

(51) Int. Cl.
*A61M 16/20* (2006.01)
*A61M 16/00* (2006.01)
*A61M 16/12* (2006.01)
*A61M 16/08* (2006.01)

(52) U.S. Cl.
CPC ...... *A61M 16/0666* (2013.01); *A61M 16/127* (2014.02); *A61M 16/20* (2013.01); *A61M 16/085* (2014.02); *A61M 16/0858* (2014.02); *A61M 16/0875* (2013.01); *A61M 2016/0027* (2013.01); *A61M 2016/0039* (2013.01); *A61M 2202/0208* (2013.01); *A61M 2205/3327* (2013.01); *A61M 2205/3334* (2013.01); *A61M 2205/52* (2013.01)

(58) Field of Classification Search
CPC .............. A61M 16/125; A61M 16/127; A61M 2016/0027; A61M 2016/0033; A61M 2016/0039; A61M 2205/3334; A61M 2205/3341; A61M 2205/3344; G01L 7/00
See application file for complete search history.

(56) References Cited

U.S. PATENT DOCUMENTS

| | | | |
|---|---|---|---|
| 7,080,645 B2 | 7/2006 | Genger et al. | |
| 7,562,659 B2 | 7/2009 | Matarasso | |
| 9,995,645 B2* | 6/2018 | Allum | A61M 16/0051 |
| 2002/0029004 A1 | 3/2002 | Starr et al. | |
| 2004/0118403 A1* | 6/2004 | O'Connor | A61M 16/0051 |
| | | | 128/204.23 |
| 2006/0011198 A1 | 1/2006 | Matarasso | |
| 2006/0180149 A1* | 8/2006 | Matarasso | A61M 16/06 |
| | | | 128/204.18 |
| 2009/0044805 A1 | 2/2009 | Somaiya et al. | |
| 2009/0241952 A1 | 10/2009 | Nicolazzi et al. | |
| 2010/0078024 A1 | 4/2010 | Andrieux et al. | |
| 2010/0252037 A1* | 10/2010 | Wondka | A61M 16/0003 |
| | | | 128/203.12 |
| 2010/0269827 A1 | 10/2010 | Rapoport | |
| 2012/0232420 A1* | 9/2012 | Salamitou | A61B 5/087 |
| | | | 600/538 |
| 2012/0247471 A1 | 10/2012 | Masic et al. | |
| 2012/0325211 A1 | 12/2012 | Allum et al. | |
| 2013/0118496 A1 | 5/2013 | Truschel et al. | |
| 2013/0192600 A1 | 8/2013 | Eklund et al. | |
| 2013/0331726 A1 | 12/2013 | Weber | |
| 2014/0000610 A1* | 1/2014 | Rapoport | A61M 16/0069 |
| | | | 128/204.23 |
| 2014/0144441 A1 | 5/2014 | Martin et al. | |
| 2014/0283834 A1* | 9/2014 | Ahmad | A61M 16/0006 |
| | | | 128/204.23 |
| 2014/0305431 A1 | 10/2014 | Holley et al. | |
| 2015/0000660 A1 | 1/2015 | Martin | |
| 2015/0250973 A1 | 9/2015 | Allum et al. | |
| 2015/0265787 A1 | 9/2015 | O'Connor et al. | |
| 2015/0335851 A1 | 11/2015 | Cullen et al. | |

\* cited by examiner (SIDE VIEW)

(TOP VIEW)

TECHNIQUES FOR DETERMINING PATIENT AIRWAY PRESSURE

CROSS-REFERENCE TO RELATED APPLICATIONS

This application is a continuation of the co-pending U.S. patent application titled, "TECHNIQUES FOR DETERMINING PATIENT AIRWAY PRESSURE," filed on Oct. 17, 2014 and having Ser. No. 14/517,186, which claims the priority benefit of the U.S. provisional patent application titled, "DETERMINING PATIENT AIRWAY PRESSURE," filed on Oct. 18, 2013 and having Ser. No. 61/893,000. The subject matter of these related applications is hereby incorporated herein by reference.

BACKGROUND OF THE INVENTION

Field of the Invention

Embodiments of the present invention relate generally to ventilators and, more specifically, to techniques for determining patient airway pressure.

Description of the Related Art

A conventional ventilator is a mechanical device configured to move air into and out of the lungs of a user. The ventilator is typically coupled to an interface that is worn by the user, such as a tracheostomy tube, endotracheal tube, nasal mask or face mask, or nasal cannula. When the user inhales, the ventilator detects inspiration and pumps air through a delivery tube to the interface in order to create a positive pressure within that interface. The positive pressure forces air into the lungs of the user to assist with inhaling. When the user exhales, the ventilator detects expiration and allows air out of the delivery tube to reduce the pressure within the interface to allow exhalation.

Accurately determining the positive pressure generated within the interface during ventilation is critical in order for the ventilator to provide the prescribed therapy to the patient, limit excessive airway pressures and to provide indicative alarms to the user/clinician if the ventilator is not delivering the set pressure. Excessive pressures could be detrimental to the health of the user. For this reason, conventional ventilators usually employ some form of sensor configured to determine interface pressure or proximal airway pressure.

For example, designs could include a pressure transducer within the interface. The pressure transducer is linked to the ventilator and configured to report the measured pressure to the ventilator. If the interface pressure exceeds a maximum value, then the ventilator alerts the user. One problem with this type of design is that pressure transducers are bulky and therefore increase the size and weight of interfaces, potentially making these interfaces uncomfortable for the user. Another problem is that pressure transducers are generally far too bulky to be used in smaller nasal interfaces, and so users are required to rely on mask-type interfaces that cover the mouth and nose.

In view of these limitations, most designs place the pressure sensor proximate to the ventilator and then couple the pressure sensor to the interface via a secondary lumen, known in the art as the "sense tube." The sense tube propagates pressure changes to the pressure transducer, which can then detect the interface pressure. This design is problematic, though, because adding a secondary lumen complicates the tubing between the ventilator and the user. One technique for simplifying such tubing is to integrate the sense tube directly into the delivery tube. However, such a design is generally too costly to implement.

As the foregoing illustrates, what is needed in the art is a more effective technique for determining the pressure within a ventilator interface.

SUMMARY OF THE INVENTION

One embodiment of the present invention sets forth a computer-implemented method for estimating the pressure of a gas within an interface, including determining a first relationship between a measurable quantity associated with the gas and the pressure of the gas within the interface, generating a first measurement of the measurable quantity associated with the gas, and estimating the pressure of the gas within the interface based on the first relationship and the first measurement.

At least one advantage of the various designs and techniques set forth herein is that the disclosed ventilator does not require additional pressure transducers or extra lumen in order to accurately determine the pressure of compressed gas delivered to the user, thereby reducing the cost and complexity of the ventilator as a whole.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

In the following description, numerous specific details are set forth to provide a more thorough understanding of the present invention. However, it will be apparent to one of skill in the art that the present invention may be practiced without one or more of these specific details. In other instances, well-known features have not been described in order to avoid obscuring the present invention.

In the following disclosure, a ventilator is described that assists a user with breathing while eliminating the need for extraneous sensors and tubing normally found in prior art ventilators. In particular, the ventilator described herein relies on a predetermined relationship between a measurable quantity associated with a compressed gas and the maximum pressure of that compressed gas upon delivery to the user. Based on the predetermined relationship, control logic within the ventilator is capable of accurately determining the pressure of the gas delivered to the user. When the desired pressure is not achieved, the control logic initiates corrective action to change the pressure of the compressed gas.

System Overview

Figure 1:
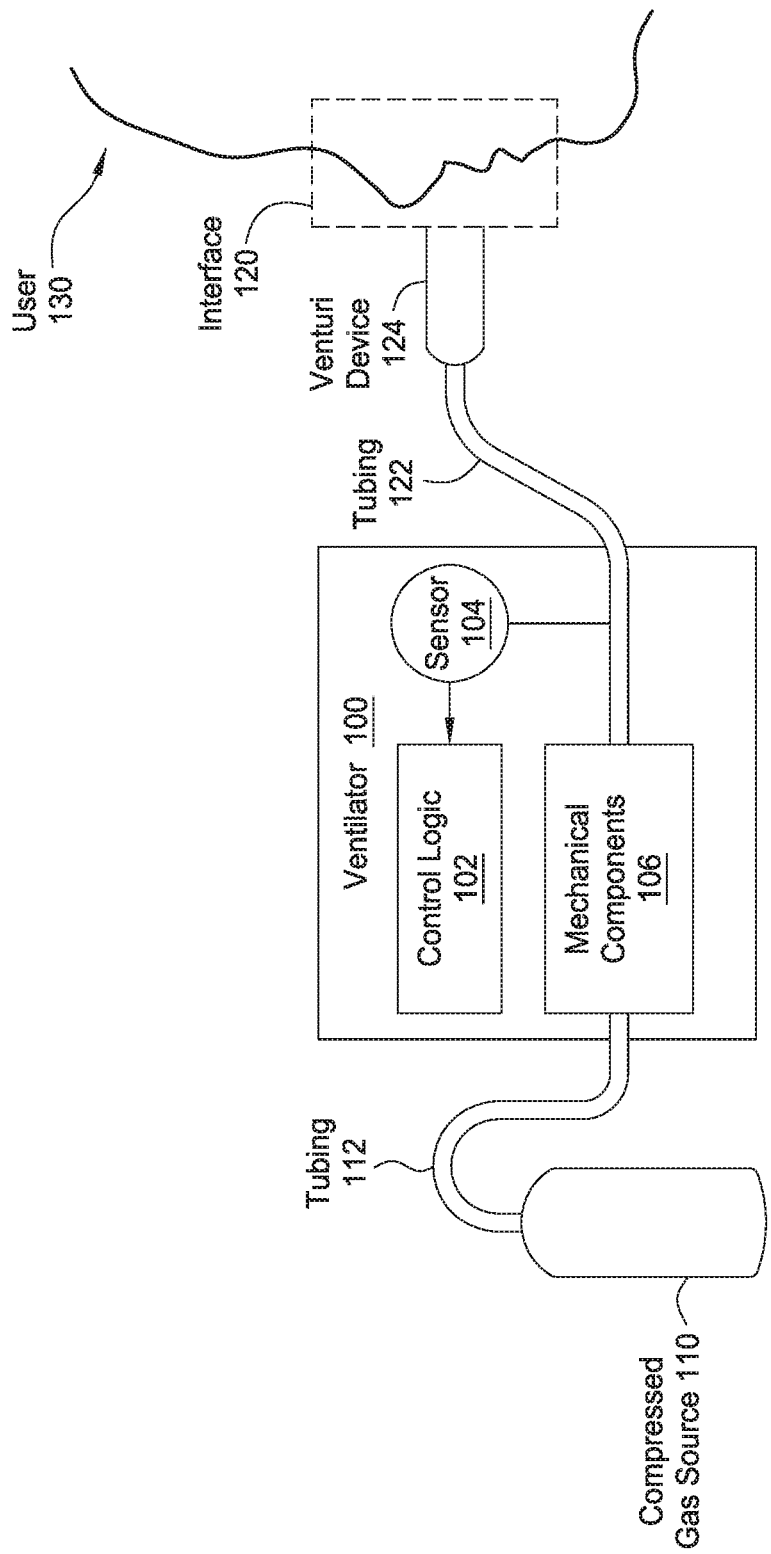
FIG. 1 illustrates a ventilator coupled between a compressed gas source and an interface worn by a user, according to one embodiment of the present invention.

FIG. 1 illustrates a ventilator 100 coupled between a compressed gas source 110 and an interface 120 worn by a user 130, according to one embodiment of the present invention. As shown, ventilator 100 is coupled to compressed gas source 110 via tubing 112 and coupled to interface 120 via tubing 122 and venturi device 124. Compressed gas source 110 may include pressurized oxygen or pressurized air. In operation, ventilator 100 is configured to receive the compressed gas from compressed gas source 110 via tubing 112, and to then provide compressed gas to interface 120, when the user inhales, via tubing 122 and venturi device 124. The compressed gas generates a positive pressure within interface 120 to assist user 130 with breathing. In one embodiment, ventilator 100 may also generate a negative pressure within interface 120, when user 130 exhales, to assist user 130 with exhalation. The specific techniques for detecting inhalation and exhalation are well known and outside the scope of the present disclosure.

As also shown, ventilator 100 includes control logic 102, sensor 104, and mechanical components 106. Control logic 102 is coupled to sensor 104. Mechanical components 106 are coupled between tubing 112 and tubing 122. Tubing 112 is coupled to an inlet associated with mechanical components 106, and tubing 122 is coupled to an outlet associated with mechanical components 106. Sensor 104 is coupled to tubing 122 at the outlet of mechanical components 106.

Control logic 102 includes electronic circuitry configured to process sensor readings and user input, and, in response, to generate control signals for managing the operation of ventilator 100 as a whole. Control logic 102 may be an application-specific integrated circuit (ASIC), a central processing unit (CPU) coupled to memory, and so forth.

Sensor 104 includes one or more sensing devices configured to measure physical properties of compressed gas exiting mechanical components 106. Sensor 104 provides these measurements to control logic 106. Sensor 104 may include a mass flow sensor, a pressure transducer, or any other technically feasible type of gas measurement device.

Mechanical components 106 include machinery configured to regulate the flow of compressed gas received via tubing 112 for output via tubing 122. Mechanical components 106 may include pressure regulators, pumps, valves, and other mechanical devices typically associated with ventilators. Mechanical components 106 generally operate in response to control logic 102 and/or input received from user 130.

As mentioned above, ventilator 100 provides compressed gas to interface 120 via tubing 122 and venturi device 124. Venturi device 124 modifies the flow of compressed gas in order to entrain atmospheric air for delivery to user 130. In doing so, venturi device 124 introduces gas into interface 120 with a particular pressure that is referred to herein as the "interface pressure." That interface pressure may depend on the cross-sectional area of venturi device 124, among other things.

As described in greater detail below in conjunction with FIGS. 3A-4, control logic 102 is configured to estimate a maximum value for the interface pressure based on sensor readings gathered by sensor 104. Those sensor readings reflect a measurable quantity of the compressed gas. The measurable quantity may reflect any property, feature, or attribute of the compressed gas that can be measured and/or quantified. In one embodiment, the measurable quantity may be a mass flow rate of the compressed gas, as described below in conjunction with FIG. 3A. In another embodiment, the measurable quantity is a lumen pressure associated with tubing 122 that transports the compressed gas, as described below in conjunction with FIG. 3B. When the estimated maximum interface pressure is outside of a defined range or window of pressures, control logic 102 initiates corrective action to alter the interface pressure, thereby promoting proper pressure delivery to and safeguarding the user 130.

Figure 2A:
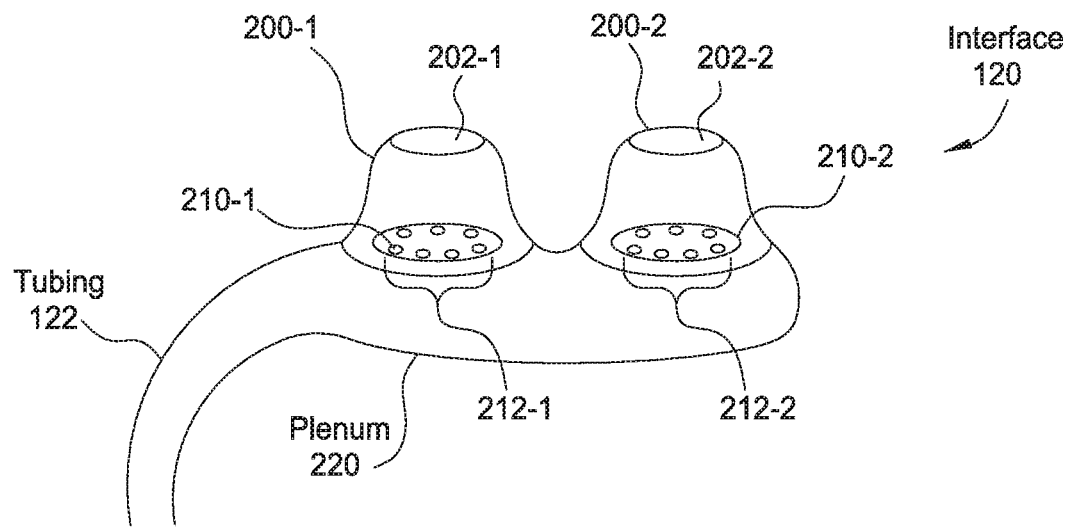
FIGS. 2A-2C illustrate different views of various implementation of the interface of FIG. 1 and associated components, according to one embodiment of the present invention.
Figure 2B:
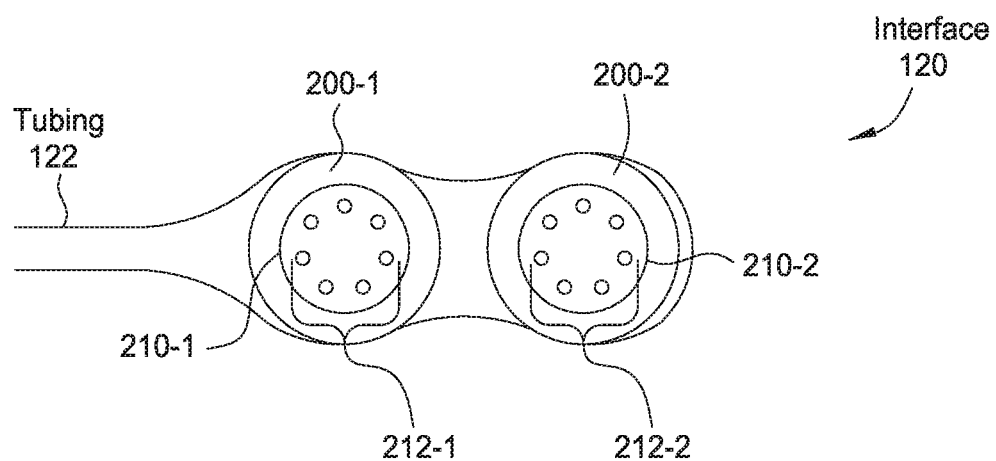

In some embodiments, interface 120 includes a plenum and specialized outlets configured to normalize the pressure of the compressed gas prior to delivery to user 130. With such a design, the accuracy with which control logic 102 estimates the maximum interface pressure may be increased. FIGS. 2A-2B illustrate an exemplary interface 120 configured to include the aforementioned elements.

Exemplary Patient Interface and Venturi Device

FIG. 2A illustrates a side view of a nasal interface that may be used to implement interface 120 of FIG. 1, according to one embodiment of the present invention. The nasal interface shown in FIGS. 2A-2B may be coupled to venturi device 124, as shown in FIG. 1. Venturi device 124 is described in greater detail below in conjunction with FIG. 2C. As shown, interface 120 includes nasal inserts 200-1 and 200-2, outlet discs 210-1 and 210-2, and plenum 220. Nasal inserts 200-1 and 200-2 include ports 202-1 and 202-2, respectively. Outlet discs 210-1 and 210-2 include outlet holes 212-1 and 212-2, respectively. Plenum 220 is coupled to tubing 122. Outlet discs 210 are coupled to plenum 220. Outlet holes 212 within outlet discs 210 are fluidly coupled to ports 212 within nasal inserts 200.

In operation, nasal inserts 200 are inserted into the nostrils of user 130. Ventilator 100 forces compressed air through tubing 122 into plenum 220. Plenum 220 is configured to buffer the received compressed gas. Outlet holes 212 within outlet discs 210 allow a flow of compressed gas from plenum 220 that depends on the size and number of those outlet holes. Compressed gas exiting plenum 220 flows through ports 202 and into the nostrils of user 130, thereby assisting with inhalation.

FIG. 2B illustrates a top view of the nasal interface shown in FIG. 2A, which, again, may be used to implement interface 120 of FIG. 1, according to one embodiment of the present invention. As shown, outlet holes 212-1 and 212-2 are disposed radially around the perimeter of outlet discs 210-1 and 210-2, respectively, although other patterns of outlet holes 212 also fall within the scope of the present invention.

When compressed gas flows through interface 120, plenum 220 and outlet holes 212 stabilize the pressure of compressed gas provided to user 130, thereby making that pressure more predictable. Among other things, the distribution of outlet holes 212 averages out variations in different properties of the compressed gas over time, including pressure and velocity, thereby delivering compressed gas with relatively consistent physical properties compared to conventional interfaces.

Accordingly, control logic 102 shown in FIG. 1 may estimate the maximum pressure within interface 120 based on readings gathered by sensor 104 with greater accuracy. Again, control logic 102 is configured to estimate the maximum pressure within interface 120 based on a predetermined relationship between those sensor readings and the maximum pressure associated with interface 120. That predetermined relationship may be further improved when venturi device 124 is implemented, as described in greater detail below in conjunction with FIG. 2C.

Figure 2C:
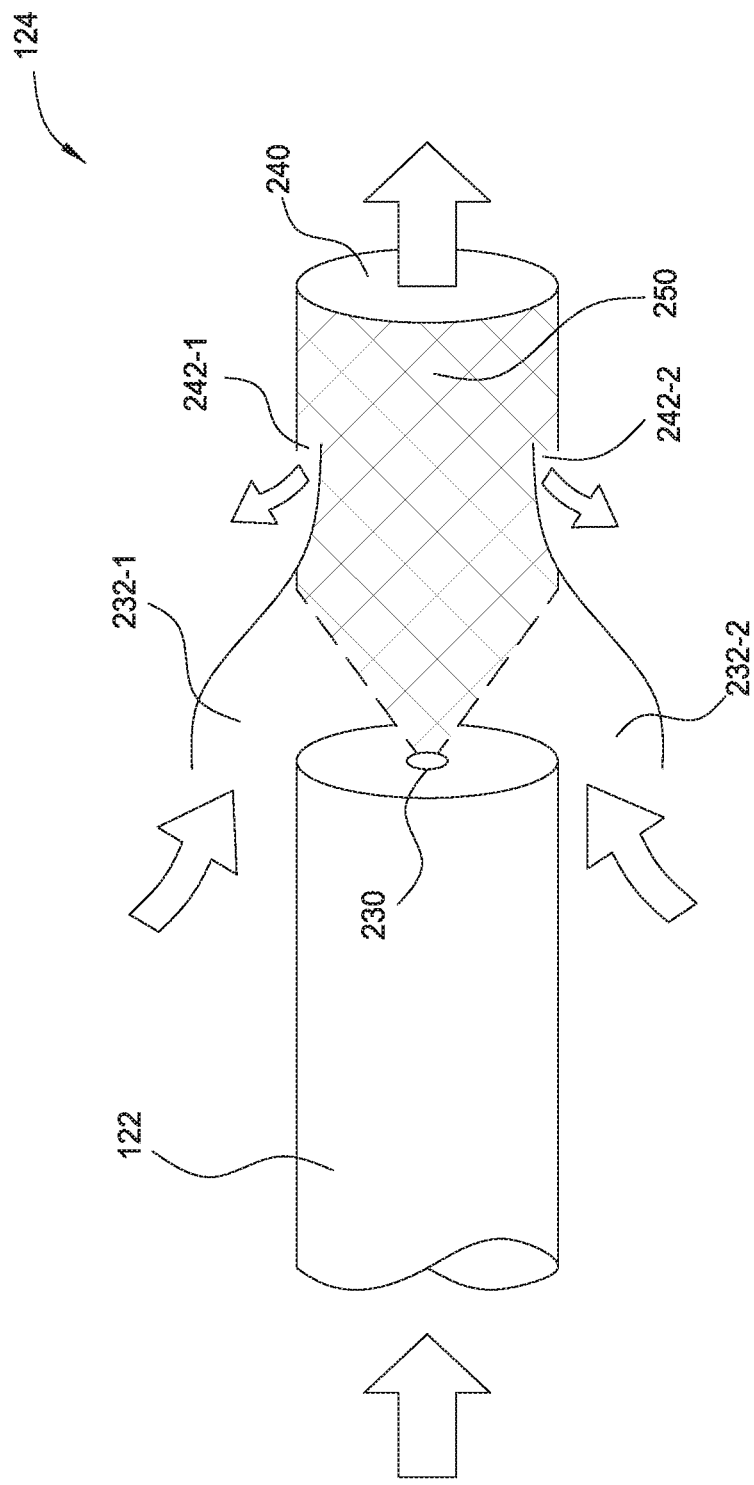

FIG. 2C illustrates venturi device 124 of FIG. 1 in greater detail, according to one embodiment of the present invention. As shown, venturi device 124 is coupled to tubing 122 and includes outlet 230 and port 240. Venturi device 124 is configured to provide gas 250 with a particular airway pressure that depends on the geometry of venturi device 124. Specifically, as also shown, venturi device 124 includes entrainment ports 232-1 and 232-2 coupled proximate to outlet 230. During inhalation, gas flows through tubing 122 and outlet 230, and entrainment ports 232 then entrain atmospheric air to induce the airway pressure associated with gas 250. In addition, venturi device 124 also includes exhalation ports 242-1 and 242-2 coupled proximal to port 240. During exhalation, exhalation ports 242 allow gas to escape form venturi device 124. In various other embodiments, venturi device 124 may include similar elements as shown in FIG. 2A-2B, including outlet discs 210 that include outlet holes 212.

Venturi device 124 may be coupled to a mask-type interface, nasal interface (such as that shown in FIGS. 2A-2B), or any other type of interface 120, in order to allow user 130 to breathe through to ambient air. This capacity may significantly reduce the pressure swing in airway pressure for a given lumen flow rate. Additionally, the pressure swing due to the breathing effort of user 130 may be significantly reduced as the area of outlet 230 is reduced. With this approach, the mean airway pressure may be a relatively predictable a function of the fixed venturi geometry and the lumen flow rate. Accordingly, implementing venturi 124 in conjunction with interface 120 may increase the degree to which maximum interface pressure may be estimated based on readings gathered by sensor 104. FIGS. 3A-3B, described in greater below, discuss alternative techniques for estimating maximum interface pressure.

Determining Maximum Interface Pressure

Figure 3A:
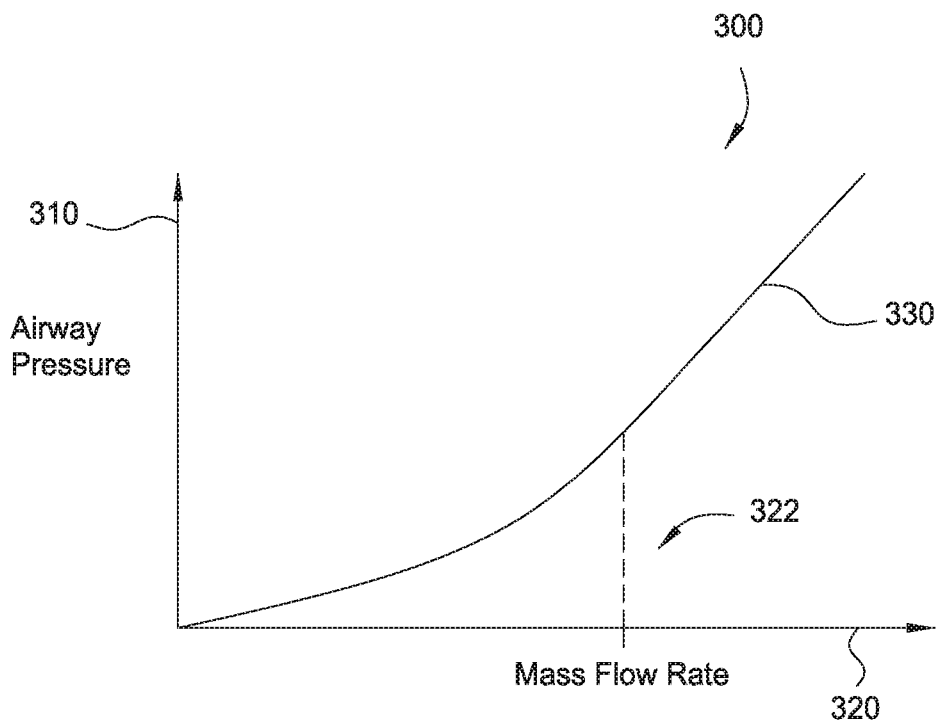
FIGS. 3A-3B are graphs that illustrate different relationships between measurable properties of a compressed gas and the maximum pressure of the compressed gas within the interface of FIG. 1, according to various embodiments of the present invention.

FIG. 3A is a graph 300 that illustrates a relationship between mass flow rate of the compressed gas and the maximum pressure of that gas within interface 120 of FIG. 1, according to one embodiment of the present invention. As shown, graph 300 includes airway pressure axis 310 and mass flow rate axis 320. Plot 330 reflects airway pressure as a function of mass flow rate. Sonic threshold 322 represents a particular mass flow rate associated with a transition from a sub-sonic to a sonic flow regime. When the mass flow rate is below threshold 322, plot 330 is approximately a squared relationship. When mass flow rate is greater than or equal to threshold 322, plot 330 is approximately linear.

The data shown in graph 300 reflects one possible relationship between a measurable quantity of compressed gas exiting ventilator 100 and the pressure of compressed gas within interface 120. In the embodiment discussed herein conjunction with FIG. 3A, that measurable quantity is mass flow rate. In operation, control logic 102 is configured to obtain a measurement of mass flow rate from sensor 104, and then compute an estimate for the maximum possible pressure within interface 120 based on the relationship indicated in graph 300. As mentioned in conjunction with FIGS. 2A-2B, outlet discs 210 and plenum 220 may buffer the flow of compressed gas through interface 120 in such a way that improves the accuracy with which graph 300 reflects to the physical dynamics of the compressed gas. Additionally, as described above in conjunction with FIG. 2C, the presence of venturi device 124 may further improve that accuracy.

Graph 300 may be constructed based on a mathematical analysis of ventilator 100 and associated components, by starting with the equation for force produced by a jet of compressed gas:

$$F = \dot{m}_{outlets} \times V_{outlets} \quad \text{(Equation 1)}$$

Equation 1 can be expanded by substituting the force variable with pressure times area associated with interface 120:

$$P_{mask} \times A_{mask} = \dot{m}_{outlets} \times V_{outlets} \quad \text{(Equation 2)}$$

Equation 2 may be solved to derive the pressure within interface 120, $P_{mask}$. $A_{max}$ is the area of the ports 202 or port 240. A correction factor, C, is incorporated to allow for interface design inefficiencies:

$$P_{mask} = \frac{\dot{m}_{outlets} \times V_{outlets}}{C \times A_{mask}} \quad \text{(Equation 3)}$$

Conceptually, Equation 3 indicates that the interface pressure is proportional to mass flow rate. Due to the presence of venturi device 124, as the mass flow rate increases, the velocity of the outlets of compressed gas increases in equal proportion up to threshold 322. As a result, the pressure within interface 120 is a function of the mass flow rate squared in the sub-sonic flow regime. Beyond threshold 322, the velocity will not increase as mass flow rate increases. In this case, the pressure in the mask will increase linearly with mass flow rate in the sonic flow regime.

With the approach described above, the relationship shown in graph 300 may be determined analytically by deriving Equation 3. That relationship may then used by control logic 102 to estimate the maximum pressure within interface 120 based on a mass flow reading provided by sensor 104.

In addition, the relationship shown in graph 300 may also be determined based on an empirical analysis of the operation of ventilator 100 and associated components. In particular, during a data-gathering process, interface 120 may be subject to a range of mass flow rates, and a sensor (not shown) within interface 120 may record a pressure reading for each different flow rate. A data set, such as a look-up table, may then be constructed that reflects a mapping between mass flow rate and interface pressure. Control logic 102 may be preprogrammed with this data set, and, during operation, control logic 102 may then estimate interface pressure by accessing the data set based on mass flow rate measurements provided by sensor 104.

As a general matter, the relationship depicted in graph 300 may be used to accurately estimate the pressure of compressed gas within interface 120, thereby obviating a need for additional sensors within interface 120 or additional sense tubing coupled to interface 120. Accordingly, the cost of ventilator 100 and associated components may be lower than conventional ventilators. FIG. 3B describes another approach to estimating interface pressure.

Figure 3B:
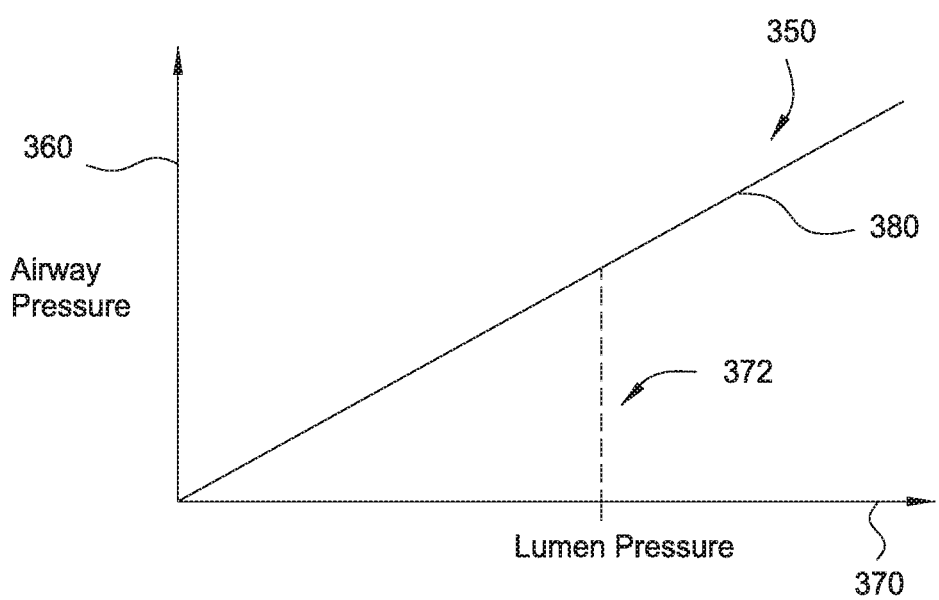

FIG. 3B is a graph 350 that illustrates a relationship between lumen pressure of the compressed gas and the maximum pressure of that gas within interface 120 of FIG. 1, according to one embodiment of the present invention. As shown, graph 350 includes airway pressure axis 360 and lumen pressure axis 370. Plot 380 reflects airway pressure as a function of lumen pressure within tubing 122 at the outlet of mechanical components 106. Sonic threshold 372 represents a particular lumen pressure associated with a transition from a sub-sonic to a sonic flow regime. Plot 380 is approximately linear for both sub-sonic and sonic flow regimes.

The data shown in graph 350 reflects another possible relationship between a measurable quantity of compressed gas exiting ventilator 100 and the pressure of compressed gas within interface 120. In the embodiment discussed herein conjunction with FIG. 3B, that measurable quantity is lumen pressure within tubing 122 at the outlet of mechanical components 106. In operation, control logic 102 is configured to obtain a measurement of lumen pressure from sensor 104, and then compute an estimate for the maximum possible pressure within interface 120 based on the relationship indicated in graph 350. As mentioned in conjunction with FIGS. 2A-2B, outlet discs 210 and plenum 220 may buffer the flow of compressed gas through interface 120 in such a way that improves the accuracy with which graph 350 reflects to the physical dynamics of the compressed gas. Additionally, as described above in conjunction with FIG. 2C, the presence of venturi device 124 may further improve that accuracy.

Graph 350 may be constructed based on a mathematical analysis of ventilator 100 and associated components, by starting with known relationships associated with venturi device 124. Venturi devices in general typically have a fixed cross-sectional area out of which compressed gas exits (shown as outlet 230 in FIG. 2C). Accordingly, the velocity of compressed gas associated with venturi device 124, and the amount of backpressure generated in the delivery lumen coupled to that venturi device, for a given mass flow rate, depends on the cross-sectional area of outlet 230 of venturi device 124. Accordingly, the pressure within the delivery lumen coupled to venturi device 124 can be described by Equation 4:

$$P_{lumen} \propto \frac{\dot{m}_{outlets}^2}{A_{outlets}} \quad \text{(Equation 4)}$$

Revisiting Equation 3, the mask pressure is proportional to the square of the venturi mass flow rate at flows less than or equal to sonic flow, since, as mentioned, mass flow rate and velocity increase in approximately proportional fashion:

$$P_{mask} \propto \frac{\dot{m}_{outlets}^2}{A_{ports}} \text{ if Flow} \le \text{sonic} \quad \text{(Equation 5)}$$

Equations 4 and 5 may be combined to provide Equation 6:

$$P_{mask} \propto \frac{P_{lumen} \times A_{outlets} \times C}{A_{ports}} \quad \text{(Equation 6)}$$

Conceptually, Equation 6 indicates that the pressure generated by the venturi device is linearly proportional to the pressure within the lumen. This relationship generally holds true for increasing mass flow rates in the sub-sonic and sonic flow regimes. One advantage of the relationship described by Equation 6 is that this relationship is linear, and so any potential errors in lumen pressure measurement result in errors of equivalent magnitude in maximum pressure estimation for the entire pressure range. Additionally, measuring pressure may be more economical than mass flow rate measurements, and so the approach described in conjunction with FIG. 3B may be less costly than that described above in conjunction with FIG. 3A.

With the approach described above, the relationship shown in graph 350 may be determined analytically by deriving Equation 6. That relationship may then be used by control logic 102 to estimate the maximum pressure within interface 120 based on a mass flow reading provided by sensor 104.

In addition, the relationship shown in graph 350 may also be determined based on an empirical analysis of the operation of ventilator 100 and associated components. Specifically, during a data-gathering process, interface 120 may be subject to a range of lumen pressures, and a sensor within interface 120 may record an interface pressure reading for each different lumen pressure. A data set, such as a look-up table, may then be constructed that reflects a mapping between lumen pressure and interface pressure. Control logic 102 may be preprogrammed with this data set, and, during operation, may then estimate interface pressure by accessing the data set based on lumen pressure measurements provided by sensor 104.

As a general matter, the relationship depicted in graph 350 may be used to accurately estimate the pressure of compressed gas within interface 120, thereby obviating a need for additional sensors within interface 120 or additional sense tubing coupled to interface 120. Accordingly, the cost of ventilator 100 and associated components may be lower than conventional ventilators.

Referring generally to FIG. 3A-3B, persons skilled in the art will recognize that the aforementioned techniques are provided for exemplary purposes to illustrate the general concept of estimating interface pressure based on a measurable quantity associated with the compressed gas output by mechanical components 106 within ventilator 100. This technique is described in stepwise fashion below in conjunction with FIG. 4.

Figure 4:
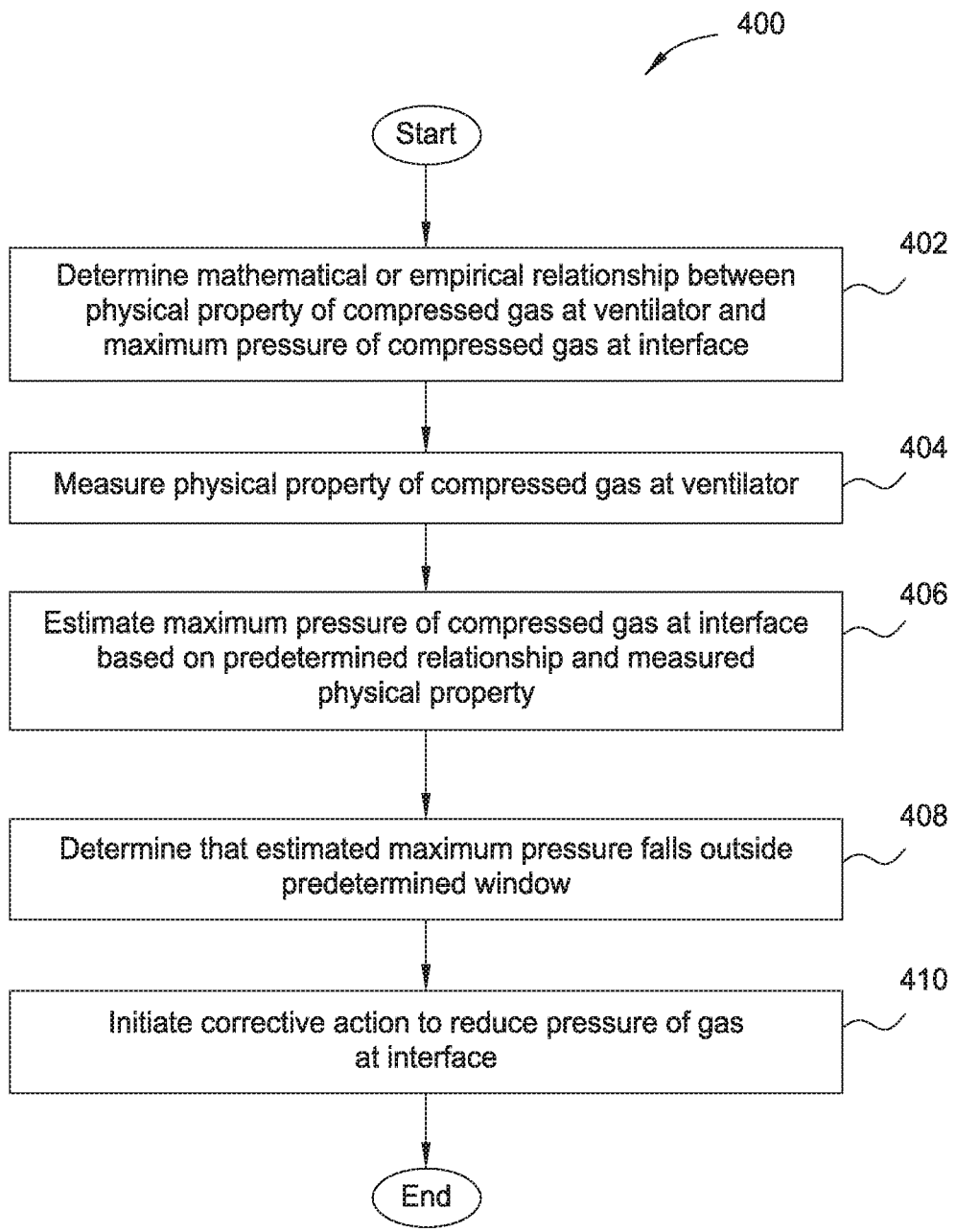
FIG. 4 is a flow diagram of method steps for determining the maximum pressure of compressed gas delivered to a user via an interface, according to one embodiment of the present invention.

FIG. 4 is a flow diagram of method steps for determining the maximum pressure of compressed gas delivered to a user via an interface, according to one embodiment of the present invention. Although the method steps are described in conjunction with the systems of FIGS. 1-3B, persons skilled in the art will understand that any system configured to perform the method steps, in any order, is within the scope of the present invention.

As shown, a method 400 begins at step 402, where control logic 102 within ventilator 100 determines a mathematical or empirical relationship between a measurable quantity of compressed gas output by mechanical components 106 and the maximum pressure of compressed gas at interface 120. In one embodiment, control logic 102 may receive data indicating the mathematical relationship, such as an equation that relates the measurable quantity to the maximum pressure. In an alternative embodiment, control logic 102 receives data that reflects a mapping, such as a look-up table, indicating a correspondence between empirical measurements of the measurable quantity and empirical measurements of the maximum pressure. In further embodiments, control logic 102 receives a mathematical relationship that is derived to fit empirical data. The measurable quantity of the compressed gas may be any attribute of the compressed gas that can be detected by sensor 104, including a mass flow rate associated with the compressed gas or a lumen pressure associated with that compressed gas, among others.

At step 404, sensor 104 within ventilator 100 measures the measurable quantity of the compressed gas exiting mechanical components 106. Again, the measurable quantity may be, among others, a mass flow rate, as described above in conjunction with FIGS. 1 and 3A, or a lumen pressure, as described above in conjunction with FIGS. 1 and 3B.

At step 406, control logic 102 estimates the maximum pressure of the compressed gas at interface 120 based on the relationship established at step 402 and the measurable quantity measured at step 404. In embodiments where control logic 102 relies on a mathematical relationship, control logic 102 may compute the output of the mathematical relationship as a function of the measured quantity. In embodiments where control logic 102 relies on an empirical mapping, control logic 102 may retrieve an estimated maximum pressure value from the empirical mapping based on the measured quantity. The accuracy of either such relationship may depend on the presence of plenum 220 and/or inlet discs 210 shown in FIGS. 2A-2B, and/or venturi device 124 shown in FIGS. 1 and 2C.

At step 408, control logic 102 determines that the maximum pressure estimated at step 406 departs from a pre-defined window of acceptable pressures. The threshold value generally reflects a pressure limit beyond which usage of interface 120 may be unsafe for user 130.

At step 410, control logic 102 initiates corrective action to adjust the pressure of the compressed gas at interface 120. In doing so, control logic 102 may alert user 130 that the ventilator pressure should be reduced or increased, or may actively reduce or increase the ventilator pressure without user intervention. The method 400 then ends.

In sum, a ventilator is configured to assist a user with breathing, while eliminating the need for extraneous sensors and tubing normally found in prior art ventilators. The ventilator relies on a predetermined relationship between a measurable quantity associated with a compressed gas and the maximum pressure of that compressed gas upon delivery to the user. The measurable quantity may be mass flow rate of the compressed gas or pressure within a delivery lumen used to transport the compressed gas, among others. Based on the predetermined relationship, the ventilator determines whether the pressure of compressed gas delivered to the user exceeds a maximum allowable pressure. When the maximum pressure is exceeded, the ventilator initiates corrective action to reduce the pressure of the compressed gas.

At least one advantage of the various designs and techniques set forth herein is that the disclosed ventilator does not require additional pressure transducers or extra lumen in order to accurately determine the pressure of compressed gas delivered to the user, thereby reducing the cost and complexity of the ventilator as a whole. In addition, since the disclosed interface does not require extraneous sensing components, the overall size and weight of the interface can be reduced, potentially increasing comfort for the user. Accordingly, the disclosed ventilator can be safely used with a low-profile nasal interfaces, further increasing comfort for the user.

While the foregoing is directed to embodiments of the present invention, other and further embodiments of the invention may be devised without departing from the basic scope thereof, and the scope thereof is determined by the claims that follow.

The invention claimed is:

1. A method for estimating a pressure of a gas within an interface, the method comprising:
   determining a first relationship between a measurable quantity associated with the gas upon exit from a ventilator and a maximum pressure of the gas within the interface, wherein the interface is disposed on a first side of a venturi device, and the gas flowing through the venturi device is at sonic flow;
   generating, at a first location within the ventilator, a first measurement of the measurable quantity associated with the gas upon exit from the ventilator, wherein the first location resides on a second side of the venturi device; and
   estimating a first maximum pressure of the gas within the interface based on the first relationship and the first measurement.

2. The method of claim 1, wherein determining the first relationship comprises establishing a mathematical relationship between the measurable quantity and the maximum pressure of the gas within the interface based on geometry associated with the interface.

3. The method of claim 1, wherein determining the first relationship comprises establishing an empirical relationship between the measurable quantity and the maximum pressure of the gas within the interface based on a plurality of measurements of the measurable quantity and a plurality of measurements of the maximum pressure of the gas within the interface.

4. The method of claim 1, wherein the measurable quantity comprises a mass flow rate associated with the gas upon exit from the ventilator.

5. The method of claim 1, wherein the measurable quantity comprises a lumen pressure value associated with the gas upon exit from the ventilator.

6. The method of claim 1, further comprising alerting a user of the interface that the pressure of the gas should be adjusted.

7. The method of claim 1, wherein the interface is configured to buffer gas entering the interface prior to delivery to a user.

8. The method of claim 7, wherein the interface includes a plenum configured to buffer pressure variations as the gas enters the interface.

9. The method of claim 8, wherein the interface further includes an outlet disc that includes a plurality of outlet holes through which gas escapes from the plenum for delivery to the user.

10. A ventilator configured to estimate a pressure of a gas within an interface coupled to the ventilator, the ventilator comprising:
    a sensor configured to generate, at a first location, a first measurement of a measurable quantity associated with the gas upon exit from the ventilator, wherein the first location resides on a first side of a venturi device; and
    control logic configured to:
      determine a first relationship between the measurable quantity associated with the gas upon exit from the ventilator and a maximum pressure of the gas within the interface, wherein the interface is disposed on a second side of the venturi device, receive the first measurement, and estimate a first maximum pressure of the gas within the interface based on the first relationship and the first measurement.

11. The ventilator of claim 10, wherein the control logic is configured to determine the first relationship by establishing a mathematical relationship between the measurable quantity and the maximum pressure of the gas within the interface based on geometry associated with the interface.

12. The ventilator of claim 10, wherein the control logic is configured to determine the first relationship by establishing an empirical relationship between the measurable quantity and the maximum pressure of the gas within the interface based on a plurality of measurements of the measurable quantity and a plurality of measurements of the maximum pressure of the gas within the interface.

13. The ventilator of claim 10, wherein the measurable quantity comprises a mass flow rate or a lumen pressure value associated with the gas upon exit from the ventilator.

14. The ventilator of claim 10, wherein the control logic is further configured to alert a user of the interface that the pressure of the gas should be adjusted.

15. A system, comprising:

an interface configured to deliver a first quantity of gas to a user; and a ventilator that is coupled to the interface and includes:
a sensor configured to generate, at a first location, a first measurement of a measurable quantity associated with the gas within the ventilator, wherein the first location resides on a first side of a venturi device; and control logic configured to:
determine a first relationship between the measurable quantity associated with the gas within the ventilator and a maximum pressure of the gas within the interface, wherein the interface is disposed on a second side of the venturi device, receive the first measurement, and estimate a first maximum pressure of the gas within the interface based on the first relationship and the first measurement.

16. The system of claim 15, wherein the interface includes:

a plenum that is fluidly coupled to the ventilator and configured to buffer the gas as the gas enters the interface; and at least one outlet disc coupled to the plenum and configured to allow the gas to escape from the plenum for delivery to the user.

17. The system of claim 16, wherein the plenum is configured to buffer the gas to equalize pressure variations as the gas enters the interface.

18. The system of claim 16, wherein the at least one outlet disc includes a plurality of outlet holes through which buffered gas escapes for delivery to the user.

19. The system of claim 15, wherein the control logic is further configured to estimate the first maximum pressure of the gas within the interface with an accuracy that depends on an equalization of pressure variations as the gas enters the interface.

20. The system of claim 15, wherein the measurable quantity comprises a mass flow rate or a lumen pressure value associated with the gas upon exit from the ventilator.

* * * * *